United States Patent [19]
Baxter et al.

[11] Patent Number: 6,090,840
[45] Date of Patent: Jul. 18, 2000

[54] PEPTIDYL COMPOUNDS HAVING MMP AND TNF INHIBITORY ACTIVITY

[75] Inventors: Andrew Douglas Baxter; David Alan Owen; John Gary Montana; Robert John Watson; John Fraser Keily, all of Cambridge, United Kingdom

[73] Assignee: Darwin Discovery Limited, United Kingdom

[21] Appl. No.: 09/155,696

[22] PCT Filed: Apr. 4, 1997

[86] PCT No.: PCT/GB97/00959

§ 371 Date: Oct. 5, 1998

§ 102(e) Date: Oct. 5, 1998

[87] PCT Pub. No.: WO97/37974

PCT Pub. Date: Oct. 16, 1997

[30] Foreign Application Priority Data

Apr. 4, 1996 [GB] United Kingdom .................... 9607249

[51] Int. Cl.[7] ...................... A61K 31/4035; C07D 209/48
[52] U.S. Cl. ........................... 514/417; 514/625; 548/477; 564/192; 564/200
[58] Field of Search ............................ 548/477; 514/417, 514/625; 564/192, 200

[56] References Cited

FOREIGN PATENT DOCUMENTS

95/13289  5/1995  WIPO .

*Primary Examiner*—Laura L. Stockton
*Attorney, Agent, or Firm*—Saliwanchik, Lloyd & Saliwanchik

[57] ABSTRACT

The subject invention concerns mercaptoalkylacyl compounds of formula (I):

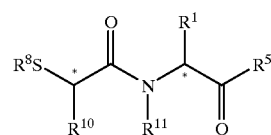

The compounds of the subject invention can be used to inhibit matrix metalloproteinases and/or TNFα- and L-selectin sheddase-mediated diseases including degenerative diseases and cancers. The subject invention also concerns methods of using the compounds of the invention to treat or prevent conditions associated with matrix metalloproteinases or that are mediated by TNFα or L-selectin sheddase.

5 Claims, No Drawings

PEPTIDYL COMPOUNDS HAVING MMP AND TNF INHIBITORY ACTIVITY

This application is a 371 of PCT/GB97/00959 filed Apr. 4, 1997.

FIELD OF THE INVENTION

This invention relates to a novel class of peptidyl derivatives, to processes for their preparation, and to their use in medicine.

BACKGROUND TO THE INVENTION

Metalloproteinases, including matrix metalloproteinase (MMP), (human fibroblast) collagenase, gelatinase, and TNF convertase (TACE),, and their modes of action, and also inhibitors thereof and their clinical effects, are described in WO-A-9611209, PCT/GB96/02438 and PCT/GB96/02892, the contents of which are incorporated herein be reference. MMP inhibitors may also be useful in the inhibition of other mammalian metalloproteinases such as the adamalysin family (or ADAMS) whose members include TNF convertase (TACE) and ADAM-10, which can cause the release of TNFα from cells, and others, which have been demonstrated to be expressed by human articular cartilage cells and also involved in the destruction of myelin basic protein, a phenomenon associated with multiple sclerosis.

Compounds which have the property of inhibiting the action of metalloproteinases involved in connective tissue breakdown, such as collagenase, stromelysin and gelatinase, have been shown to inhibit the release of TNF both in vitro and in vivo. See Gearing et al (1994), Nature 370:555–557; McGeehan et al (1994), Nature 370:558–561; GB-A-2268934; and WO-A-9320047. All of these reported inhibitors contain a hydroxamic acid zinc-binding group, as do the imidazole-substituted compounds disclosed in WO-A-9523790. Other compounds that inhibit MMP and/or TNF are described in WO-A-9513289, WO-A-9611209, WO-A-96035687, WO-A-96035711, WO-A-96035712 and WO-A-96035714.

SUMMARY OF THE INVENTION

The invention encompasses novel mercaptoalkylacyl compounds of formula (I) which are useful inhibitors of matrix metalloproteinases and/or TNFα-mediated diseases including degenerative diseases (such as defined above) and certain cancers.

Novel compounds according to the invention are of general formula (I):

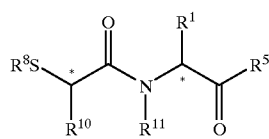

wherein:

$R^1$ is a $C_{1-6}$ alkyl, $C_{2-6}$ alkenyl, aryl, $C_{1-6}$ alkyl-aryl, heteroaryl, $C_{1-6}$ alkyl-heteroaryl, cyclo($C_{3-6}$) alkyl, $C_{1-6}$ alkyl-cyclo($C_{3-6}$)alkyl, heterocyclo($C_{4-6}$alkyl, $C_{1-6}$ alkyl-heterocyclo($C_{4-6}$)alkyl, $C_{1-6}$ alkyl-COR$^2$, or $C_{1-6}$ alkyl-AR$^3$ group where A is O, NR$^3$ or S(O)$_n$ where n=0–2 and R$^3$ is H, $C_{1-4}$ alkyl, aryl, heteroaryl, $C_{1-4}$ alkyl-aryl or $C_{1-4}$ alkyl-heteroaryl; if A=NR$^3$ the groups R$^3$ may be the same or different;

$R^2$ is OR$^4$ or N(R$^4$)$_2$ where each R$^4$ may be the same or different;

$R^4$ is H or $C_{1-4}$ alkyl;

$R^5$ is aryl (optionally substituted with R$^6$), heteroaryl (optionally substituted with R$^6$), $C_{1-4}$ alkyl-aryl (optionally substituted with R$^6$), $C_{1-4}$ alkyl-heteroaryl (optionally substituted with R$^6$), $C_{1-4}$ alkyl (optionally substituted with R$^6$), cyclo($C_{3-6}$) alkyl (optionally substituted with R$^6$), $C_{1-4}$ alkyl-cyclo($C_{3-6}$)alkyl (optionally substituted with R$^6$), heterocyclo($C_{4-6}$)alkyl (optionally substituted with R$^6$) or $C_{1-4}$ alkyl-heterocyclo($C_{4-6}$)alkyl (optionally substituted with R$^6$);

$R^6$ is halogen, $C_{1-6}$ alkyl, aryl, heteroaryl, AR$^3$, NR$^3$R$^7$, COR$^9$, SO$_2$N(R$^3$)$_2$ where each R$^3$ may be the same or different, CO$_2$R$^4$, CON(R$^3$)$_2$ where each R$^3$ may be the same or different, amidine or guanidine;

$R^7$ is COR$^{20}$, CO$_2$R$^{19}$, SO$_2$R$^9$ or CO(NR$^3$)$_2$ where each R$^3$ may be the same or different;

$R^8$ is H or COR$^9$;

$R^9$ is $C_{1-4}$ alkyl, aryl, heteroaryl, $C_{1-4}$ alkyl-aryl or $C_{1-4}$ alkyl-heteroaryl;

$R^{10}$ and $R^{11}$ are the same or different and are each H, $C_{1-6}$ alkyl (optionally substituted with R$^{12}$), aryl (optionally substituted with R$^{12}$), $C_{1-6}$ alkyl-aryl (optionally substituted with R$^{12}$), heteroaryl (optionally substituted with R$^{12}$), $C_{1-6}$ alkyl-heteroaryl (optionally substituted with R$^{12}$), cyclo ($C_{3-6}$) alkyl (optionally substituted with R$^{12}$), $C_{1-6}$ alkyl-cyclo($C_{3-6}$)alkyl (optionally substituted with R$^{12}$), heterocyclo($C_{4-6}$)alkyl (optionally substituted with R$^{12}$) or $C_{1-4}$ alkyl-heterocyclo($C_{4-6}$)alkyl (optionally substituted with R$^{12}$);

$R^{12}$ is SO$_2$R$^9$, SO$_2$(NR$^3$)$_2$ where each R$^3$ may be the same or different, SR$^8$, COR$^{13}$, N(R$^3$)$_2$ were each R$^3$ may be the same or different, NR$^3$R$^{14}$, OR$^3$, phthalimido or the groups:

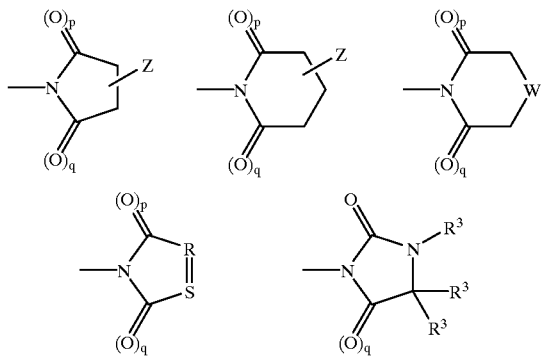

p and q are each 0 or 1 and may be the same or different;
R and S are each CH or N and may be the same or different;
W is O, S(O)$_n$ where N=0–2, or NR$^{15}$;
Z is H or $C_{0-4}$ alkyl-R$^{18}$ and may be attached to any available position on the ring;
$R^{13}$ is OR$^{20}$, N(R$^3$)$_2$ where R$^3$ may be the same or different, $C_{1-4}$ alkyl, aryl, $C_{1-4}$ alkyl-aryl, heteroaryl or $C_{1-4}$ alkyl-heteroaryl;
$R^{14}$ may be any group defined in R$^7$ or COR$^{16}$;
$R^{15}$ is H, $C_{1-4}$ alkyl, COR$^9$, CO$_2$R$^{19}$, CON(R$^3$)$_2$ where each R$^3$ may be the same or different, or SO$_2$R$^9$;
$R^{16}$ is $C_{1-4}$ alkyl-R$^{17}$;
$R^{17}$ is CO$_2$R$^4$, CON(R$^3$)$_2$ where each R$^3$ may be the same or different, N(R$^3$)$_2$ where each R$^3$ may be the same or different, SO$_2$R$^9$ or the groups:

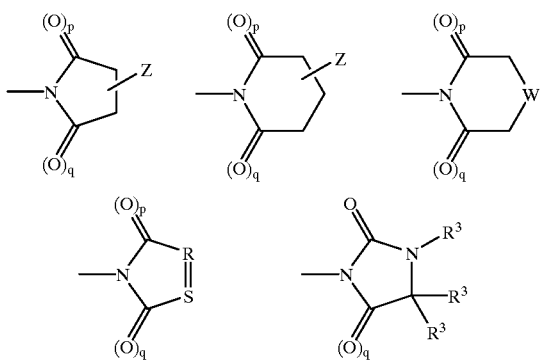

$R^{18}$ is $CO_2R^3$, $CON(R^3)_2$ where $R^3$ may be the same or different, $N(R^3)_2$ where $R^3$ may be the same or different, $NHCO_2R^{19}$, $NHSO_2R^9$ $NHCONHR^9$ or $NHCOR^9$;

$R^{19}$ is $C_{1-4}$ alkyl, $C_{1-4}$ alkyl-aryl or $C_{1-4}$ alkyl-heteroaryl; and $R^{20}$ is H, $C_{1-4}$ alkyl, $C_{1-4}$ alkyl-aryl or $C_{1-4}$ alkyl-heteroaryl; and the salts, solvates and hydrates thereof.

Combinations of substituents and/or variables are only permissible if such combinations result in stable compounds.

DESCRIPTION OF THE INVENTION

Preferred compounds of the invention are those wherein any one or more of the following apply:

$R^1$ is $C_{1-6}$ alkyl or $C_{1-6}$ alkyl-$AR^3$, $C_{1-6}$ alkyl $COR^2$ or $C_{1-6}$ alkylaryl;

$R^2$ is $OR^4$ or $N(R^4)_2$;

$R^3$ is O or $S(O)_{0-2}$;

$R^4$ is H or $C_{1-4}$ alkyl;

$R^5$ is aryl (optionally substituted with $R^6$) or heteroaryl (optionally substituted with $R^6$);

$R^6$ is $AR^3$ or aryl;

$R^9$ is $C_{1-4}$ alkyl or aryl;

$R^{10}$ or $R^{11}$ are the same or different and are each H, $C_{1-6}$ alkyl (optionally substituted with $R^{12}$), $C_{1-6}$ alkylaryl or $C_{1-6}$ alkylheteroaryl;

$R^{12}$ is $COR^{13}$, phthalimido, succinimido or 3,4,4-trimethylhydantoin;

$R^{13}$ is $OR^{20}$ or $N(R^3)_2$; and $R^{20}$ is H or $C_{1-4}$ alkyl.

The compounds of the Examples are particularly preferred.

It will be appreciated that the compounds according to the invention can contain one or more asymmetrically substituted carbon atoms, for example those marked with an asterisk in formula (I). The presence of one or more of these asymmetric centres in a compound of formula (I) can give rise to stereoisomers, and in each case the invention is to be understood to extend to all such stereoisomers, including enantiomers and diastereomers, and mixtures including racemic mixtures thereof.

In the formula herein, the ~ line is used at a potential asymmetric centre to represent the possibility of R- and S-configurations, the < line and the . . . line to represent a unique configuration at an asymmetric centre.

As used in this specification, alone or in combination, the term "$C_{1-6}$ alkyl" refers to straight or branched chain alkyl moiety having from one to seven carbon atoms, including for example, methyl, ethyl, propyl, isopropyl, butyl, tert-butyl, pentyl, hexyl and the like.

The term "$C_{1-4}$ alkyl" refers to a straight or branched chain alkyl moiety having from one to four carbon atoms, including for example, methyl, ethyl, propyl, isopropyl, butyl, tert-butyl and the like.

The term "$C_{2-6}$ alkenyl" refers to a straight or branched chain alkyl moiety having two to six carbon atoms and having in addition one double bond, of either E or Z stereochemistry where applicable. This term would include for example, vinyl, 1-propenyl, 1- and 2- butenyl, 2- methyl-2-propenyl etc.

The term "cyclo($C_{3-6}$)alkyl" refers to a saturated alicyclic moiety having from three to six carbon atoms and includes for example cyclopropyl, cyclobutyl, cylcopentyl, cyclohexyl and the like.

The term "heterocyclo ($C_{4-6}$) alkyl" refers to a saturated heterocyclic moiety having from three to six carbon atoms and one or more heteroatom from the group N, O, S and includes for example azetidinyl, pyrrolidinyl, tetrahydrofuranyl, piperidinyl and the like.

The term "aryl" means an optionally substituted phenyl or naphthyl group with the substituent(s) being selected, for example, from halogen, trifluoromethyl, $C_{1-6}$ alkyl, alkoxy, phenyl and the like.

The term "heteroaryl" refers to aromatic ring systems of five to ten atoms or which at least one atom is selected from the group, O, N, or S and includes for example furanyl, thiophenyl, pryidyl, indolyl, quinolyl and the like.

The term "halogen" means fluorine, chlorine, bromine or iodine.

The terms "protected amino" and "protected carboxy" mean amino and carboxy groups which are protected in a manner familiar to those skilled in the art. For example, an amino group can be protected by a benzyloxycarbonyl, tert-butoxycarbonyl, acetyl or like groups, or in the form of a phthalimido or like group. A carboxyl group can be protected in the form of a readily cleavable ester such as the methyl, ethyl, benzyl or tert-butyl ester.

Salts of compounds of formula (I) include pharmaceutically acceptable salts, for example acid addition salts derived from inorganic or organic acids, such as hydrochlorides, hydrobromides, p-toluenesulphonates, phosphates, sulphates, perchlorates, acetates, trifluoroacetates, propionates, citrates, malonates, succinates, lactates, oxalates, tartrates and benzoates.

Salts may also be formed with bases. Such salts include salts derived from inorganic or organic bases, for example alkali metal salts such as magnesium or calcium salts, and organic amine salts such as morpholine, piperidine, dimethylamine or diethylamine salts.

When the "protected carboxy" group in compounds of the invention is an esterified carboxyl group, it may be a metabolically labile ester of formula $CO_2R^{21}$ where $R^{21}$ may be an ethyl, benzyl, phenethyl, phenylpropyl, α- or β-naphthyl, 2,4-dimethylphenyl, 4-tert-butylphenyl, 2,2,2-trifluoroethyl, 1-(benzyloxy)benzyl, 1-(benzyloxy)ethyl, 2-methyl-1-propionyloxypropyl, 2,4,6-trmethylbenzyloxymethyl or pivaloyloxymethyl group.

Compounds of the general formula (I) may be prepared by any suitable method known in the art and/or by the following processes.

It will be appreciated that where a particular stereoisomer of formula (I) is required, the synthetic processes described herein may be used with the appropriate homochiral starting material and/or isomers may be resolved from mixtures using conventional separation techniques (e.g. HPLC).

The compounds according to the invention may be prepared by the following process. In the description and formulae below the groups $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$ and $R^{21}$, A, W, X, Y and Z are as defined above, except where otherwise indicated. It will be appreciated that functional groups, such as amino, hydroxyl or carboxyl groups, present in the various compounds described below, and which it is desired to retain, may need to be in protected form before any reaction is initiated. In such instances, removal of the protecting group may be the final step in a particular reaction. Suitable protecting groups for such functionality will be apparent to those skilled in the art. For specific details see Greene et al, "Protective Groups in Organic Synthesis", Wiley Interscience.

A process for preparing compounds of general formula (I) comprises deprotecting (for example by hydrolysis) a compound of general formula (II)

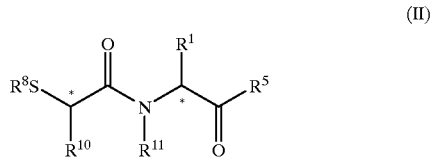

(II)

wherein $R^8$ represents a suitable protecting group (eg tert-butyl, trityl, benzoate or acetate).

It will be appreciated that where a particular stereoisomer of formula (I is required, this may be obtained by conventional resolution techniques such as high performance liquid chromatography. Where desired, however, appropriate homochiral starting materials may be used in the coupling reaction to yield a particular stereoisomer of formula (I). This is exemplified below.

Compounds of general formula (II) may be prepared by coupling of a acid of general formula (III)

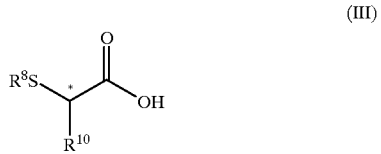

(III)

or an active derivative thereof, with an amino ketone derivative of general formula (IV)

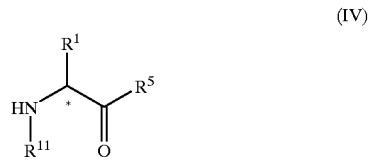

(IV)

or a protected derivative thereof, followed by removal of any protecting groups. Suitable protecting groups for the ketone moiety include acetals and thioacetals. Active derivatives of acids of formula (III) include for example acid anhydrides or acid halides, such as acid chlorides.

The coupling reaction may be performed using standard conditions for amination reactions of this type. Thus, the reaction may be achieved in a solvent, for example an inert organic solvent such as an ether, e.g. a cyclic ether such as tetrahydrofuran, an amide e.g. a substituted amide such as dimethylformamide, or a halogenated hydrocarbon such as dichloromethane at a low temperature e.g. $-30°$ C. to ambient temperature, such as $-20°$ C. to $0°$ C., optionally in the presence of as base, e.g. an organic base such as an amine, e.g. triethylamine or a cyclic amine such as N-methylmorpholine. Where an acid of formula (III) is used, the reaction may additionally be performed in the presence of a condensing agent, for example a diimide such as N,N'-dicyclohexylcarbodiimide, advantageously in the presence of a triazole such as 1-hydroxybenzotriazole. Alternatively, the acid may be reacted with a chloroformate for example ethylchloroformate, prior to reaction with the amine of formula (IV).

Particularly when $R^5$ is an aryl group, the amino ketone intermediate of general formula (IV) may be prepared by Friedel-Crafts acylation of the arene, $R^5$, with a suitably protected amino acid of general formula (V)

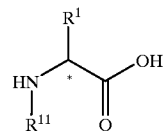

(V)

or more usually an activated derivative thereof. Suitable protecting groups for the amino acid nitrogen are alkyloxycarbonyl groups such as methoxycarbonyl or ethoxy carbonyl for example. Active derivatives of acids of formula (V) include for example acid anhydrides or acid halides, such as acid chlorides.

A more general procedure for the preparation of compounds of general formula (IV) involves the reaction of an active derivative of a suitably protected amino acid of general formula (V) with an organometallic reagent of the formula $MR^5$ (VI), wherein M is a metal such as Li or Mg, followed by removal of any protecting groups. Active derivatives of acids of formula (V) include for example acid anhydrides, acid halides, such as acid chlorides or amides such as the N(OMe)Me amide which are particularly suitable for this reaction. Suitable protecting groups for the amino acid nitrogen in compounds of general formula (V) are tert-butyloxycarbonyl (Boc) or benzyloxcarbonyl (Cbz).

Intermediates of general formula (II) may also be prepared by nucleophilc displacement by an thiol of the formula $R^8SH$ (VII) wherein $R^8$ represents a suitable protecting group (e.g. tert-butyl, trityl or acetate), prepared using standard conditions known to those skilled in the art as exemplified by WO-A-9005719, with an alkylating agent of general formula (VIII)

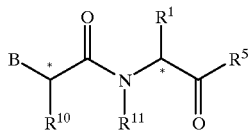

(VIII)

wherein B is a suitable leaving group (e.g. a halogen such as bromide, or an alkylsulphonate ester such as methanesulphonate).

Thiols of general formula (VII) may be obtained from commercially available starting materials using methods known to those skilled in the art. Many thiols of general formula (VII) are also commercially available.

Intermediates of general formula (VIII) may be prepared by coupling of an acid of formula (IX)

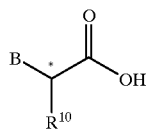

(IX)

or an active derivative thereof, with a suitable protected amino ketone of general formula (IV) using the procedure outlined previously. Active derivatives of acids of formula (IX) include for example acid anhydrides or acid halides, such as acid chlorides.

Acids of formulae (III) and (IX) may be prepared according to the procedure described in WO-A-9611209.

Amino acids and their derivatives as depicted by general formula (V) can be obtained in chiral or racemic form. In the chiral form they provide asymmetric building blocks for the chiral synthesis of compounds of general formula (I). Many of these derivatives can be readily obtained from commercially available starting materials using methods known to those skilled in the art. See "The Practice of Peptide Synthesis" by M. Bodanszk et al, Springer Verlag, New York (1984) and WO-A-9221360).

Compounds of formula (I) may also be prepared by interconversion of other compounds of formula (I). Thus, for example, a compound of formula (I) wherein $R^1$ is a $C_{1-6}$ alkyl group may be prepared by hydrogenation (using palladium on carbon in suitable solvent, such as an alcohol—e.g. ethanol) of a compound of formula (I) wherein $R^1$ is a $C_{2-6}$ alkenyl group. A further example would include a compound of formula (I) wherein $R^8$ is a group $R^9$ CO may be prepared by acylation (using a suitable acid chloride $R^9$COCl, in the presence of a base such as a triethylamine in a suitable solvent, such as a chlorinated solvent—e.g. dichloromethane) of a compound of formula (I) wherein $R^8$ is H.

Any mixtures of final products or intermediates obtained can be separated on the basis of the physico-chemical differences of the constituents, in known manner, into the pure final products or intermediates, for example by chromatography, distillation, fractional crystallization, or by formation of a salt if appropriate or possible under the circumstances.

The compounds according to the invention exhibit in vitro inhibiting activities with respect to stromelysin, collagenase and gelatinase. Compounds according to the invention also exhibit in vitro inhibition of TNF release. The activity and selectivity of the compounds may be determined by use of the appropriate enzyme inhibition test, for example as described in WO-A-9611209 or PCT/GB96/02892.

This invention also relates to a method of treatment for patients (including man and/or mammalian animals raised in the dairy, meat or fur industries or as pets) suffering from disorders or diseases which can be attributed to stromelysin as previously described, and more specifically, a method of treatment involving the administration of the matrix metalloproteinase inhibitors of formula (I) as the active constituents.

Accordingly, the compounds of formula (I) can be used among other things in the treatment of osteoarthritis and rheumatoid arthritis, and in diseases and indications resulting from the over-expression of these matrix metalloproteinases such as found in certain metastatic tumour cell lines.

As mentioned above, compounds of formula (I) are useful in human or veterinary medicine since they are active as inhibitors of TNF and MMPs. Accordingly in another aspect, this invention concerns:

a method of management (by which is meant treatment of prophylaxis) of disease or conditions mediated by TNF and/or MMPs in mammals, in particular in humans, which method comprises administering to the mammal an effective, amount of a compound of formula (I) above, or a pharmaceutically acceptable salt thereof, and a compound of formula (I) for use in human or veterinary medicine, particularly in the management (by which is meant treatment or prophylaxis) of diseases or conditions mediated by TNF and/or MMPs; and the use of a compound of formula (I) in the preparation of an agent for the management (by which is meant treatment or prophylaxis) of diseases or conditions mediated by TNF and/or MMPs.

The disease or conditions referred to above include inflammatory diseases, autoimmune diseases cancer, cardiovascular diseases, diseases involving tissue breakdown such as rheumatoid arthritis, osteoarthritis, osteoporosis, neurodegeneration, Alzheimer's disease, atherosclerosis, congestive heart failure, stroke, vasculitis, Crohn's disease, ulcerative colitis, multiple sclerosis, periodontitis, gingivitis and those involving tissue breakdown such as bone resportion, haemorrhage, coagulation, acute phase response, cachexia and anorexia, acute infections, HIV infections, fever, shock states, graft versus host reactions, dermatological conditions, surgical wound healing, psoriasis, atopic dermatitis, epidermolysis bullosa, tumour growth, angiogenesis and invasion by secondary metastases, ophthalmological disease, retinopathy, corneal ulceration, reperfusion injury, migraine, meningitis, asthma, rhinitis, allergic conjunctivitis, eczema, anaphylaxis, restenosis, congestive heart failure, endometriosis, atherosclerosis and endosclerosis.

For the treatment of rheumatoid arthritis, osteoarthritis, and in diseases and indications resulting from the over-expression of matrix metalloendoproteinases such as found in certain metastatic tumour cell lines or other diseases mediated by the matrix metalloendoproteinases or increased TNF production, the compounds of formula (I) may be administered orally, topically, parenterally, by inhalation spray or rectally in dosage unit formulations containing non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats etc, the compounds of the invention are effective in the treatment of humans.

The pharmaceutical composition containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastointestinal tract and thereby provide a sustained action over a longer period. For example, a time delay material such as glyceryl monostearate or glyeryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules where in the active ingredient is mixed with an inert solid diluent, for example calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate polyvinyl-pyrrolidone, gum tragacanth and gum acacia; dispersing or wetting agents may be a naturally occuring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such a polyoxyethylene with partial esters derived from fatty acids and hexitol anhydrides, for example polyoxyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified, for example sweetening, flavouring and colouring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occuring gums, for example gum acacia or gum tragacanth, naturally-occuring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavouring agents.

Syrups and elixirs may be formulated with sweetening agents, for example gycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be in a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc containing the compounds of Formula (I) are employed. (For purposes of this application, topical application shall include mouth washes and gargles).

Dosage levels of the order of from about 0.05 mg to about 140 mg per kilogram of body weight per day are useful in the treatment of the above-indicated conditions (about 2.5 mg to about 7 gms per patient per day). for example, inflammation may be effectively treated by the administration of from about 0.01 to 50 mg of the compound per kilogram of body weight per day (about 0.5 mg to about 3.5 gms per patient per day).

The amount of active ingredient that may be combined with the carrier materials to produce a single dosage form will vary depending upon the host treated and the particular mode of administration. For example, a formulation intended for the oral administration of humans may vary from about 5 to about 95 percent of the total composition. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet time of administration, route of administration, rate of excretion, drug combination and the severity of the particular disease undergoing therapy.

The following Examples illustrate the invention.

In the Examples, the following abbreviations are used:

| | |
|---|---|
| TNFα | Tumour Necrosis Factor α |
| LPS | Lipopolysaccharide |
| ELISA | Enzyme linked immunosorbant assay |
| EDC | 1-(Dimethylaminopropyl)-3-ethylcarbodiimide, hydrochloride |
| RT | Room Temperature |

INTERMEDIATE 1

(R)-N-[(1,1-Dimethyl)ethoxycarbonyl]-S-methylcysteine N-methoxy-N-methylamide

A solution of Boc-S-methylcysteine (5 g), N,O-dimethylhydroxylamine hydrochloride (2.28 g) and N-hydroxybenzotriazole monohydrate (3.16 g) in tetrahydrofuran (60 ml) was treated with N-methylmorpholine at 0° C. under nitrogen. EDC (4.89 g) was added and the reaction was warmed to RT and stirred for 48 hours. The reaction mixture was concentrated in vacuo, to give a colourless residue which was partitioned between ethyl acetate (100 ml) and 10% citric acid (100 ml). The organic phase was washed with saturated sodium bicarbonate (70 ml) and brine (70 ml), dried (MgSO$_4$), and evaporated to dryness in vacuo to give the title compound as a pale waxy solid (1.16 g, 29%).

TLC R$_f$ 0.52 (1:1 ethyl acetate/hexane)

Similarly prepared was:

INTERMEDIATE 2

N-[(1,1-Dimethyl)ethoxycarbonyl]-L-leucine N-methoxy-N-methylamide

From Boc-leucine, as a colourless viscous oil (43%)

TLC R$_f$ 0.61 (1:1 ethyl acetate/hexane)

INTERMEDIATE 3

(R)-N-[(1,1-Dimethyl)ethoxycarbonyl]-1-(4-methoxy phenyl)-3-(methylthio)-1-oxo-2-propylamine A solution of 4-bromoanisole (3.06 g) in anhydrous tetrahydrofuran (30 ml) at −78° C. under nitrogen was treated with 1.6 M solution of n-butyllithium in hexane (10.24 g) over 15 minutes. The mixture was stirred for 1 hour then Intermediate 1 (1.60 g) in anhydrous tetrahydrofuran (20 ml) was added dropwise over 1 hour. The reaction was stirred for 1 hour at −78° C., warmed to RT and then quenched with saturated ammonium chloride (100 ml). The mixture was extracted with diethylether (100 ml) and the organic phase dried (Na$_2$SO$_4$) and evaporated to dryness in vacuo to give a pale yellow oil. Purification by flash column chromatography on silica eluting with 20% ethyl acetate in hexane provided the title compound as a colourless viscous oil (1.24 g, 23%).

TLC R$_f$ 0.71 (1:1 ethyl acetate/hexane)

Similarly prepared was:

INTERMEDIATE 4

(R)-N-[(1,1-Dimethyl)ethoxycarbonyl]-1-(4-methoxy phenyl)-4-methyl-1-oxo-2-pentylamine From Intermediate 2 as a colourless viscous oil (39%)

TLC R$_f$ 0.75 (1:1 ethyl acetate/hexane)

INTERMEDIATE 5

(R)-1-(4-methoxyphenyl)-3-(methylthio)-1-oxo-2-propyl amine, trifluoroacetate salt A solution of Intermediate 3 (83 mg) in dichloromethane (5 ml) was cooled to 0C under nitrogen, followed by the dropwise addition of trifluoroacetic acid (6 ml). The reaction was warmed to RT and stirred for 15 hours. The reaction mixture was evaporated to dryness in vacuo, then azeotroped twice with toluene (5 ml) to provide the title compound as an orange glass (90 mg, 100%).

TLC R$_f$ 0.35 (1% ammonium hydroxide, 10% methanol in dichloromethane)

Similarly prepared was:

INTERMEDIATE 6

(R)-1-(4-methoxyphenyl)-4-methyl-1-oxo-2-pentylamine trifluoroacetate salt

From Intermediate 4, as a colourless glass

TLC R$_f$ 0.42 (1% ammonium hydroxide, 10% methanol in dichloromethane)

INTERMEDIATE 7

(S)-2-Acetylmercapto-5-phthalimidopentanoic acid

The title compound was prepared by the procedure outlined in WO 96/11209.

EXAMPLE 1

(S)-N-[2-Acetylmercapto-5-phthalimido]pentanoyl-1-(4-methoxyphenyl)-3-(methylthio)-1-oxo-(2R)-propyl amine A solution of Intermediate 5 (90 mg), Intermediate 7 (79 mg), and N-hydroxybenzotriazole monohydrate (36 mg) in anhydrous tetrahydrofuran (5 ml) at 0° C. under nitrogen was treated with EDC (52 mg) and then N-methylmorpholine (27 mg). The reaction was warmed to RT and stirred for 20 hours then evaporated to dryness in vacuo to give an orange residue, which was partitioned between ethyl acetate (20 ml) and 10% citric acid (20 ml). The organic phase was washed with saturated sodium bicarbonate (15 ml), then with brine (15 ml), dried (Na$_2$SO$_4$) and evaporated to dryness in vacuo to give a yellow oil. Purification by flash column chromatography on silica eluting with 2% methanol in dichloromethane provided the title compound as a pale yellow solid (60 mg, 46%).

TLC R$_f$ 0.28 (2% methanol in dichloromethane)

MS 529 MH+

Similarly prepared were:

EXAMPLE 2

(S)-N-[2-Acetylmercapto-5-phthalimido]pentanoyl-1-(4-methoxyphenyl)-4-methyl-1-oxo-(2R)-pentylamine From Intermediate 6 and Intermediate 7, as a white solid (52%).

TLC R$_f$ 0.35 (2% methanol in dichloromethane)

MS 525 MH$^+$

EXAMPLE 3

2-(Acetylmercapto)acetyl-1-(4-methoxyphenyl)-3-(methylthio)-1-oxo-(2R)-propylamine From Intermediate 5 and 2-(acetylmercapto)acetic acid, as a pale yellow solid (47%).

TLC R$_f$ 0.45 (2% methanol in dichloromethane)

EXAMPLE 4

2-(Acetylmercapto)acetyl-1-(4-methoxyphenyl)-4-methyl-1-oxo-(2R)-pentylamine

From Intermediate 6 and 2-(acetylmercapto)acetic acid, as a white solid (47%).

TLC R$_f$ 0.47 (2% methanol in dichloromethane)

EXAMPLE 5

(S)-N-[2-Mercapto-5-phthalimido]pentanoyl1-(4-methoxy phenyl)-3-(methylthio)-1-oxo-(2R)-propylamine A solution of Example 1 (50 mg) in methanol (5 ml) at 0° C. under nitrogen was treated with 0.880 ammonium hydroxide (0.13 ml). The reaction was warmed slowly to RT, then stirred for 4 hours. The reaction mixture was evaporated to dryness in vacuo to give a white residue. Purification by flash column chromatography on silica eluting with 3% methanol in dichloromethane provided the title compound as a white solid (20 mg, 43%).

TLC $R_f$ 0.30 (2% methanol in dichloromethane)
MS 489 MH$^{30}$
Similarly prepared were:

EXAMPLE 6

(S)-N-[2-Mercapto-5-phthalimido]pentanoyl1-(4-methoxy phenyl)-4-methyl-1-oxo-(2R)-penTylamine From Example 2, as a white solid (55%).
TLC $R_f$ 0.32 (2% methanol in dichloromethane)
MS 485 MH$^+$

EXAMPLE 7

2-Mercaptoacetyl-1-(4-methoxyphenyl)-3-(methylthio)-1-oxo-(2R)-propylamine

From Example 3, as a pale yellow solid (44%)
TLC Rf 0.31 (4% methanol in dichloromethane)
MS 300 MH$^+$

EXAMPLE 8

2-Mercaptoacetyl-1-(4-methoxyphenyl)-4-methyl-1-oxo-(2R)-pentylamine

From Example 4, as a pale yellow solid (52%).
TLC $R_f$ 0.36 (4% methanol in dichloromethane)
MS 296 MH$^+$

What is claimed is:
1. A compound of general formula (I)

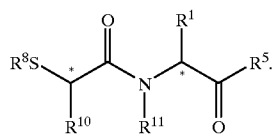

wherein:

R$^1$ is selected from the group consisting of C$_{1-6}$ alkyl, C$_{2-6}$ alkenyl, aryl, C$_{1-6}$ alkyl-aryl, heteroaryl, C$_{1-6}$ alkyl-heteroaryl,cyclo(C$_{3-6}$) alkyl, C$_{1-6}$ alkyl-cyclo (C$_{3-6}$)alkyl,heterocyclo(C$_{4-6}$)alkyl, C$_{1-6}$ alkylheterocyclo(C$_{4-6}$)alkyl, C$_{1-6}$ alkyl-COR$^2$, and C$_{1-6}$ alkyl-AR$^3$ group where A is selected from the group consisting of O, NR$^3$ and S(O)$_n$ where n=0–2 and R$^3$ is selected from the group consisting of H, C$_{1-4}$ alkyl, aryl, heteroaryl, C$_{1-4}$ alkyl-aryl and C$_{1-4}$ alkylheteroaryl; A=NR$^3$ the groups R$^3$ may be the same or different;

R$^2$ is OR$^4$ or N(R$^4$)$_2$ where each R$^4$ may be the same or different;

R$^4$ is H or C$_{1-4}$ alkyl;

R$^5$ is selected from the group consisting of aryl (optionally substituted with R$^6$), heteroaryl, (optionally substituted with R$^6$), C$_{1-4}$ alkyl-aryl (optionally substituted with R$^6$), C$_1$_alkyl-heteroaryl (optionally substituted with R$^6$), C$_{1-1}$ alkyl (optionally substituted with R$^6$), cyclo(C$_{3-6}$)alkyl (optionally substituted with R$^6$), C$_{1-4}$ alkyl-cyclo(C$_{3-6}$)alkyl (optionally substituted with R$^6$), heterocyclo(C$_{4-6}$)alkyl (optionally substituted with R$^6$) and C$_{1-4}$ alkyl-heterocyclo (C$_{4-6}$)alkyl (optionally substituted with R$^6$);

R$^6$ is selected from the group consisting of halogen, C$_{1-6}$ alkyl, aryl, heteroaryl, AR$^3$, NR$^3$R$^7$, COR$^9$, SO$_2$N(R$^3$)$_2$ where each R$^3$ may be the same or different, CO$_2$R$^4$, CON(R$^3$)$_2$ where each R$^3$ may be the same or different, amidine and guanidine;

R$^7$ is selected from the group consisting of COR$^{20}$, CO$_2$R$^{19}$, SO$_2$R$^9$ and CO(NR$^3$)$_2$ where each R$^3$ may be the same or different;

R$^8$ is H or COR$^9$;

R$^9$ is selected from the group consisting of C$_{1-4}$ alkyl, aryl, heteroaryl, C$_{1-4}$ alkyl-aryl and C$_{1-4}$ alkylheteroaryl;

R$^{10}$ and R$^{11}$ are the same or different and are each selected from the group consisting of H, C$_{1-6}$ alkyl (optionally substituted with R$^{12}$), aryl (optionally substituted with R$^{12}$), C$_{1-6}$ alkyl-aryl (optionally substituted with R$^{12}$), heteroaryl (optionally substituted with R$^{12}$), C$_{1-6}$ alkylheteroaryl (optionally substituted with R$^{12}$), cyclo (C$_{3-6}$) alkyl (optionally substituted with R$^{12}$), C$_{1-6}$ alkyl-cyclo(C$_{3-6}$)alkyl (optionally substituted with R$^{12}$), heterocyclo(C$_{4-6}$)alkyl (optionally substituted with R$^{12}$) and C$_{1-4}$ alkyl-heterocyclo(C$_{4-6}$)alkyl (optionally substituted with R$^{12}$);

R$^{12}$ is selected from the group consisting of SO$_2$R$^9$, SO$_2$(NR$^3$)$_2$ where each R$^3$ may be the same or different, SR$^8$, COR$^{13}$, N(R$^3$)$_2$ where each R$^3$ may be the same or different, NR$^3$R$^{14}$, OR$^3$, phthalimido, and the groups:

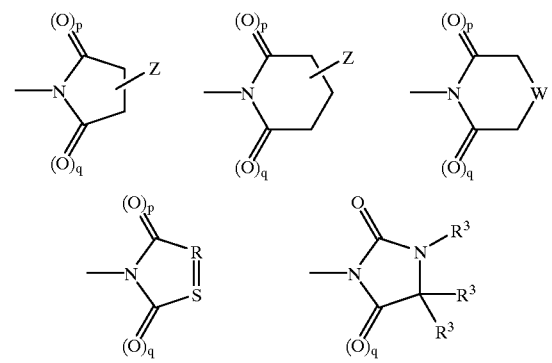

p and q are each 0 or 1 and may be the same or different;
R and S are each CH or N and may be the same or different;
W is O, S(O)$_n$ where n=0–2, or NR$^{15}$;
Z is H or C$_{0-4}$ alkyl-R$^{18}$ and may be attached to any available position on the ring;
R$^{13}$ is selected from the group consisting of OR$^{20}$, N(R$^3$)$_2$ where R$^3$ may be the same or different, C$_{1-4}$ alkyl, aryl, C$_{1-4}$ alkyl-aryl, heteroaryl and C$_{1-4}$ alkyl-heteroaryl;
R$^{14}$ may be any group defined in R$^7$ or COR$^{16}$;
R$^{15}$ is selected from the group consisting of H, C$_{1-4}$ alkyl, COR$^9$, CO$_2$R$^{19}$, CON(R$^3$)$_2$ where each R$^3$ may be the same or different, and SO$_2$R$^9$;
R$^{16}$ is C$_{1-4}$ alkyl-R$^{17}$;
R$^{17}$ is selected from the group consisting of CO$_2$R$^4$, CON(R$^3$)$_2$ where each R$^3$ may be the same or different, $N(R^3)_2$ where each $R^3$ may be the same or different, $SO_2R^9$ and the groups:

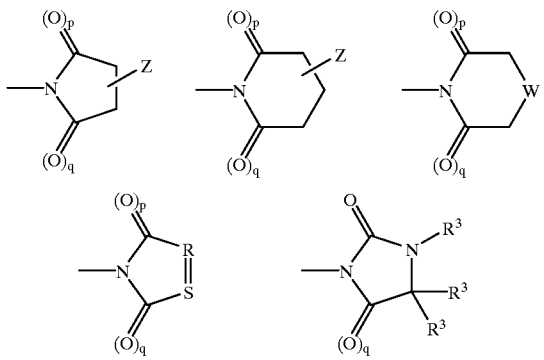

$R^{18}$ is selected from the group consisting of $CO_2R^3$, $CON(R^3)_2$ where $R^3$ may be the same or different, $N(R^3)_2$ where $R^3$ may be the same or different, $NHCO_2R^{19}$, $NHSO_2R^9$ $NHCONHR^9$ and $NHCOR^9$;

$R^{19}$ is selected from the group consisting of $C_{1-4}$ alkyl, $C_{1-4}$ alkyl-aryl and $C_{1-4}$ alkyl-heteroaryl; and $R^{20}$ is selected from the group consisting of H, $C_{1-4}$ alkyl, $C_{1-4}$ alkyl-aryl and $C_{1-4}$ alkyl-heteroaryl;

or the salt, solvate or hydrate thereof.

2. The compound according to claim 1, wherein:

$R^1$ is selected from the group consisting of $C_{1-6}$ alkyl or $C_{1-6}$ alkyl-$AR^3$, $C_{1-6}$ alkyl $COR^2$ and $C_{1-6}$ alkylaryl;

$R^2$ is $OR^4$ or $N(R^4)_2$;

$W^3$ is O or $S(O)_{0-2}$;

$R^4$ is H or $C_{1-4}$ alkyl;

$R^5$ is aryl (optionally substituted with $R^6$) or heteroaryl (optionally substituted with $R^6$);

$R^6$ is $AR^3$ is aryl;

$R^9$ is $C_{1-4}$ alkyl or aryl;

$R^{10}$ or $R^{11}$ are the same or different and are each selected from the group consisting of H, $C_{1-6}$ alkyl (optionally substituted with $R^{12}$), $C_{1-6}$ alkylaryl and $C_{1-6}$ alkyl-heteroaryl;

$R^{12}$ is selected from the group consisting of $COR^{13}$, phthalimido, succinimido and 3,4,4-trimethylhydantoin;

$R^{13}$ is $OR^{20}$ or $N(R^3)_2$; and $R^{20}$ is H or $C_{1-4}$ alkyl.

3. A compound of claim 1, selected from the group consisting of (S)-N-[2-Acetylmercapto-5-phthalimido]pentanoyl-1-(4-methoxyphenyl)-3-(methylthio)-1-oxo-(2R)-propylamine;

(S)-N-[2-Acetylmercapto-5-phthalimido]pentanoyl-1-(4-methoxyphenyl)-4-methyl-1-oxo-(2R)-pentylamine;

2-(Acetylmercapto)acetyl-1-(4-methoxyphenyl)-3-(methylthio)-1-oxo-(2R)-propylamine;

2-(Acetylmercapto)acetyl-1-(4-methoxyphenyl)-4-methyl-1-oxo-(2R)-pentylamine;

(S)-N-[2-Mercapto-5-phthalimido]pentanoyl-1-(4-methoxyphenyl)-3-(methylthio)-1-oxo-(2R)-propylamine;

(S)-N-[2-Mercapto-5-phthalimido]pentanoyl-1-(4-methoxyphenyl)-4-methyl-1-oxo-(2R)-pentylamine;

2-Mercaptoacetyl-1-(4-methoxyphenyl)-3-(methylthio)-1-oxo-(2R)-propylamine; and

2-Mercaptoacetyl-1-(4-methoxyphenyl)-4-methyl-1-oxo-(2R)-pentylamine.

4. The compound according to claim 1, in the form of a single enantiomer or diastereomer.

5. A pharmaceutical composition for use in therapy, comprising a compound according to claim 1, and a pharmaceutically-acceptable diluent, or carrier.

* * * * *

UNITED STATES PATENT AND TRADEMARK OFFICE
CERTIFICATE OF CORRECTION

PATENT NO. : 6,090,840
DATED : July 18, 2000
INVENTOR(S) : Andrew Douglas Baxter, David Alan Owen, John Gary Montana, Robert John Watson, John Fraser Keily It is certified that error appears in the above-identified patent and that said Letters Patent is hereby corrected as shown below:

Column 13,
Line 57, "A=$NR^3$" should read -- if A=$NR^3$ --.
Line 65, "$C_1$.alkyl-heteroaryl" should read -- $C_{1-4}$ alkyl-heteroaryl --.

Column 15,
Line 33, "$W^3$" should read -- W --.
Line 37, "is aryl" should read -- or aryl --.

Signed and Sealed this

Ninth Day of April, 2002

Attest:

JAMES E. ROGAN
Attesting Officer  Director of the United States Patent and Trademark Office